United States Patent [19]
Pohl et al.

[11] Patent Number: 5,698,761
[45] Date of Patent: Dec. 16, 1997

[54] COORDINATION CATALYST SYSTEMS

[75] Inventors: Ludwig Pohl, Darmstadt; Eike Poetsch, Mühltal; Herbert Schumann, Berlin; Karin Weiss, Bayreuth; Karl-Heinz Thiele, Halle; Hans-Ludwig Hirsch, Reinheim, all of Germany

[73] Assignee: Merck Patent Gesellschaft Mit Beschrankter Haftung, Darmstadt, Germany

[21] Appl. No.: 484,310

[22] Filed: Jun. 7, 1995

Related U.S. Application Data

[62] Division of Ser. No. 256,988, Jul. 29, 1994, Pat. No. 5,468,707.

[30] Foreign Application Priority Data

Dec. 1, 1992 [DE] Germany .......... 42 40 294.8
Mar. 3, 1993 [DE] Germany .......... 43 06 569.4

[51] Int. Cl.$^6$ .......... C07C 6/00
[52] U.S. Cl. .......... 585/646; 585/643; 585/645
[58] Field of Search .......... 585/643, 645, 585/646

[56] References Cited

U.S. PATENT DOCUMENTS

| | | | |
|---|---|---|---|
| 5,015,747 | 5/1991 | Hostalek et al. | 556/1 |
| 5,030,741 | 7/1991 | Erdmann et al. | 556/1 |

*Primary Examiner*—Sharon Gibson
*Attorney, Agent, or Firm*—Millen, White, Zelano & Branigan, P.C.

[57] ABSTRACT

The invention relates to the use of cyclic organometallic compounds as components in coordination catalyst systems, to corresponding coordination catalyst systems and also to processes for the preparation of polymers by coordination polymerization and of unsaturated hydrocarbons by catalyzed metathesis of alkenes and alkynes using such coordination catalyst systems.

9 Claims, No Drawings

COORDINATION CATALYST SYSTEMS

This is a division of the application Ser. No. 08/256,988 filed Jul. 29, 1994 now U.S. Pat. No. 5,468,707.

BACKGROUND OF THE INVENTION

The invention relates to coordination catalyst systems based on transition metal compounds of subgroups IV to VIII and organometallic compounds of main group III of the Periodic Table of the Elements. Such organometallic catalysts are extraordinarily versatile catalyst systems which are used in chemical reactions of and with olefinically unsaturated compounds. These are, in particular, processes for preparing olefin polymers by coordination polymerization and the metathesis of alkenes or alkynes. Of substantial industrial importance is the preparation of polyethylene, of increased density (high density polyethylene, HDPE) and of polymers and copolymers of ethylene, propylene or other 1-alkenes and alkynes. Catalyzed metathesis enables higher unsaturated hydrocarbon compounds to be prepared in a targeted way from unsymmetric alkenes or alkynes and, from unsaturated cyclic hydrocarbon compounds, makes it possible to obtain long-chain unsaturated hydrocarbons. The latter are used, for example, in the preparation of elastomers. In addition, coordination catalysts are used in further reactions, such as in the hydrogenation of alkenes or in organometallic syntheses.

In accordance with the previous scientific knowledge of the mechanism of action of coordination catalysts, it is assumed that in each case one transition metal compound forms the catalytically active center to which the olefinically unsaturated compound binds coordinately in a first step. The olefin polymerization proceeds via a coordination of the monomers and a subsequent insertion reaction into a transition metal-carbon or a transition metal-hydrogen bond. The presence of organometallic compounds in the coordination catalyst systems or during the catalyzed reaction is required to activate the catalyst or maintain its activity by reduction, with or without alkylation or formation of a complex system. These compounds are therefore also known as co-catalysts. The compound containing the catalytically active transition metal atom is known as the primary catalyst or pre-catalyst.

The best known industrially used catalyst systems for coordination polymerization are of the "Ziegler-Natta catalyst" type and of the "Phillips catalyst" type. The former comprise the reaction product of a metal alkyl or hydride of the elements of the first three main groups of the Periodic Table and a reducible compound of a transition metal element of subgroups IV to VII, the combination most frequently used comprising an aluminum alkyl, such as triethylaluminum or diethylaluminum chloride, and titanium (IV) chloride. Newer highly active Ziegler-Natta catalysts are systems in which the titanium compound is chemically fixed to the surface of magnesium compounds such as, in particular, magnesium chloride.

As Phillips catalysts, use is made of chromium compounds which undergo reduction or activation principally by organometallic compounds and are bound to inorganic supports. Cr(VI) and Cr(II) are regarded as catalytically active species ("reduced Phillips catalyst"). Here too, the co-catalysts used are principally alkylaluminum compounds and also aluminoxane compounds.

Newer developments of particularly high-performance polymerization catalysts are based on metallocene compounds. The catalysts known as "Kaminsky catalysts" are, for example, titanocene and zircononocene compounds which are cyclopentadienyl complexes of titanium or zirconium alkyls or halides and also derivatives thereof, which are activated with the aid of aluminum, boron or phosphorus trialkyls or aluminoxane.

The practical use of these catalysts and related types in the wide variety of process variants developed can give products with sometimes very different properties. For olefin polymers, which are of generally known importance as materials, usability and field of use depend as a result of properties, on the one hand, on the type of monomers on which the polymer is based or on selection and ratio of the comonomers and the typical physical parameters characterizing the polymer, such as mean molecular weight, molecular weight distribution, degree of branching, degree of crosslinking, crystallinity, density, presence of functional groups in the polymer, etc., and, on the other hand, on properties determined by the process such as the content of low-molecular-weight impurities, presence of catalyst residues and finally on the costs.

To assess the performance of a coordination catalyst system, the decisive factors are, besides the realization of the desired product properties, further factors such as the activity of the catalyst system, i.e. the amount of catalyst required for an economical conversion of a given amount of olefin, the product throughput per unit time and the product yield, the loss of catalyst and also the reusability of the catalyst. Catalyst systems are therefore sought which have as high as possible a productivity but also have a high specificity in favor of a low degree of branching and a high stereoregularity of the polymer, the latter being particularly important for polypropylene and polymers of higher 1-alkenes.

However, an essential question is also that of the stability and the handleability of the catalyst or its components. Pratically all known coordination catalysts are extremely sensitive to air and moisture. Exposure to (atmospheric) oxygen and/or water reduces or irreversibly destroys the activity of known coordination catalysts. Reduced Phillips catalysts, for example, immediately glow on exposure to air and are then unusable. The coordination catalysts therefore have to be strictly protected from exposure to air and moisture during preparation, storage and use, which naturally makes handling more difficult and increases the outlay required.

Conventional catalyst systems are also sensitive to materials which contain electron-rich elements such as oxygen or nitrogen. Compounds such as alcohols and amines, or even polar monomers which can be of interest as comohomers or additives for the polymer, deactivate the catalyst.

Even more sensitive in this respect and therefore even more difficult to handle are the organometallic compounds to be used as activators or cocatalysts, such as, in particular, the alkylaluminum compounds predominantly used for this purpose. Precisely these pose a serious problem in practice because of their extreme sensitivity and pyrophoric nature.

There was therefore a particular need to find less sensitive organometallic compounds which are nevertheless suitable as activating components in coordination catalyst systems. These substitute compounds should be able to make coordination catalyst systems having at least the same application properties and, if possible, an even greater breadth of use accessible. These themselves should in turn have a lower sensitivity and therefore less problematical handleability.

SUMMARY OF THE INVENTION

It has now been found that cyclic organometallic compounds of the formulae I or II

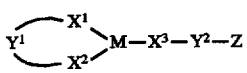

(I)

in which

M is B, Al, Ga, In,

X¹, X², X³ are, in each case independently of one another, CHR¹, NR², O, S,

Y¹, Y² are, in each case independently of one another, —(CH₂)ₘ—, o-(CH₂)ₚ—C₆H₄—(CH₂)_q—, o-(CH₂)ₚ—C₆H₆—(CH₂)_q—, o-(CH₂)ₚ—C₆H₈—(CH₂)_q—, o-(CH₂)ₚ—C₆H₁₀—(CH₂)_q—, o-(CH₂)ₚ—C₅H₄—(CH₂)_q—, o-(CH₂)ₚ—C₅H₆—(CH₂)_q—, o-(CH₂)ₚ—C₅H₈—(CH₂)_q—, —(CH₂)ₚ—CH=CH—(CH₂)_q—, is NR³R⁴, PR³R⁴, OR⁵, SR⁵, R¹ is H, OH, halogen, $C_{1-6}$-alkyl or $C_{1-6}$-alkoxy, $C_{5-7}$-cycloalkyl, phenyl, R², R³, R⁴, R⁵ are, in each case independently of one another, H or $C_{1-6}$-alkyl, $C_{5-7}$-cycloalkyl, phenyl, R³ and R⁴ together also a $C_{4-6}$-alkylene bridge, m is a number from 1 to 6, p, q are, in each case independently of one another, a number from 0 to 2,

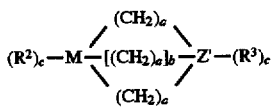

(II)

having M, R² and R³ as defined above and in which

Z' is N, P, a is a number from 2 to 4, b, c are the numbers 0 or 1 with b+c=1, are particularly suitable as components in coordination catalyst systems.

The invention accordingly provides for the use of cyclic organometallic compounds of the formulae I or II as components in coordination catalyst systems.

The invention provides, in particular, for the use of these compounds as components in coordination catalyst systems for the coordination polymerization and metathesis of alkenes and alkynes.

The invention further provides coordination catalyst systems based on transition metal compounds of subgroups IV to VIII and organometallic compounds of main group III of the Periodic Table of the Elements, with these containing at least one compound of the formula I or II.

The invention additionally provides processes for preparing polymers by coordination polymerization and for preparing unsaturated hydrocarbon compounds by a catalyzed metathesis reaction, in which processes the coordination catalyst systems used are those containing at least one compound of the formula I or II.

The compounds of the formulae I and II have a cyclic structure in which the group IIIa element boron (B), aluminum (Al), gallium (Ga) and indium (In) is in every case a member of a ring system.

In formula I, the group IIIa element M forms a metallocyclic ring together with the groups X¹, Y¹ and X². In the simplest case the ring is closed by an alkylene group having a total of from 3 to 8 carbon atoms. The groups X¹ and X² adjacent to M can be an amino group, oxygen or sulfur. In other cases, Y¹ comprises an aromatic, an aliphatic or an unsaturated aliphatic ring having 5 or 6 carbon atoms and linked in the ortho position or a C-C double bond preferably having a cis configuration. A carbon atom adjacent to the metal atom can also bear a substituent R¹ which can be OH, halogen such as, in particular, F, Cl and Br, $C_{1-6}$-alkyl, $C_{1-6}$-alkoxy, $C_{5-7}$-cycloalkyl or phenyl. A carbon atom substituted in this way is then a center of chirality in the molecule. In such a case, formula I represents the racemic mixture and also the corresponding enantiomers or diastereomers in their pure forms. The third bond of the metal atom M bears, linked via a spacer grouping X³-Y², a group Z containing a heteroatom. X³ can be a CH₂ group, O, S or an amino group optionally substituted by $C_{1-6}$-alkyl, $C_{5-7}$-cycloalkyl or phenyl. Y² is, in the simplest case, an alkylene group having from 1 to 6 carbon atoms. In the other cases, Y² comprises an aromatic, an aliphatic or an unsaturatedly aliphatic ring having 5 or 6 carbon atoms and linked in the ortho position or a C-C double bond preferably having a cis configuration. Z comprises the heteroatoms N, P, O or S in the form of an amino, a phosphino, hydroxy or thiol group, in each case optionally substituted by $C_{1-6}$-alkyl, with two such alkyl radicals also being able to form an alkylene bridge, or $C_{5-7}$-cycloalkyl or phenyl.

In formula II, the metal atom M forms a monocyclic or bicyclic ring system via two or three alkylene bridges, which can each contain from 2 to 4 carbon atoms, together with the heteroatom Z' which can be N or P. In the case of a monocyclic ring system, the bonds of M and Z' which are still free in each case are occupied by H or $C_{1-6}$-alkyl, $C_{5-7}$-cycloalkyl or phenyl.

The compounds of the formula I and II are stabilized intramolecularly by electron transfer from the nitrogen, phosphorus, oxygen or sulfur atom to the electron-deficient IIIa element. In comparison with conventional metal alkyls, they therefore possess high stability towards (atmospheric) oxygen and moisture. They are not pyrophoric and therefore easy to handle. This stabilization is attributable to the intramolecular coordinate bond.

Typical examples of compounds of the formula I are:
1-Alumina-1-(4-dimethylaminobutyl)cyclobutane
1-Alumina-1-(2-dimethylaminoethyl)cyclopentane
1-Alumina-1-(2-diethylaminoethyl)cyclopentane
1-Alumina-1-(2-dipropylaminoethyl)cyclopentane
1-Alumina-1-(2-diisopropylaminoethyl)cyclopentane
1-Alumina-1-(2-dibutylaminoethyl)cyclopentane
1-Alumina-1-(3-dimethylaminopropyl)cyclopentane
1-Alumina-1-(3-diethylaminopropyl)cyclopentane
1-Alumina-1-(3-dipropylaminopropyl)cyclopentane
1-Alumina-1-(3-diisopropylaminopropyl)cyclopentane
1-Alumina-1-(3-dibutylaminopropyl)cyclopentane
1-Alumina-1-(4-dimethylaminobutyl)cyclopentane
1-Alumina-1-(4-diethylaminobutyl)cyclopentane
1-Alumina-1-(4-dipropylaminobutyl)cyclopentane
1-Alumina-1-(4-diisopropylaminobutyl)cyclopentane
1-Alumina-1-(4-dibutylaminobutyl)cyclopentane
1-Alumina-1-(3-dimetylaminopropyl)-2-methylcyclopentane
1-Alumina-1-(2-dimethylaminoethyl)cyclohexane
1-Alumina-1-(2-diethylaminoethyl)cyclohexane
1-Alumina-1-(2-dipropylaminoethyl)cyclohexane
1-Alumina-1-(2-diisopropylaminoethyl)cyclohexane
1-Alumina-1-(2-dibutylaminoethyl)cyclohexane
1-Alumina-1-(3-dimethylaminopropyl)cyclohexane, b.p. 70°–73° C./0.01 mbar
1-Alumina-1-(3-diethylaminopropyl)cyclohexane, b.p. 98° C./0.6 mbar
1-Alumina-1-(3-dipropylaminopropyl)cyclohexane
1-Alumina-1-(3-diisopropylaminopropyl)cyclohexane
1-Alumina-1-(3-dibutylaminopropyl)cyclohexane
1-Alumina-1-(4-dimethylaminobutyl)cyclohexane
1-Alumina-1-(4-diethylaminobutyl)cyclohexane 1-Alumina-1-(4-dipropylaminobutyl)cyclohexane
1-Alumina-1-(4-diisopropylaminobutyl)cyclohexane
1-Alumina-1-(4-dibutylaminobutyl)cyclohexane
1-Alumina-1-(o-diethylaminobenzyl)cyclopentane
1-Alumina-1-(o-diethylaminobenzyl)cyclohexane
1-Alumina-1-(o-diisopropylaminobenzyl)cyclohexane
1-Alumina-1-(3-dimethylaminopropyl)-2-methylcyclohexane
1-Alumina-1-(2-o-dimethylaminophenylethyl)cyclopentane
1-Alumina-1-(2-o-diethylaminophenylethyl)cyclobutane
1-Galla-1-(3-dimethylaminopropyl)cyclobutane
1-Galla-1-(2-dimethylaminoethyl)cyclopentane
1-Galla-1-(3-dimethylaminopropyl)cyclopentane
1-Galla-1-(2-dimethylaminoethyl)cyclopentane
1-Galla-1-(2-diethylaminoethyl)cyclopentane
1-Galla-1-(2-dipropylaminoethyl)cyclopentane
1-Galla-1-(2-diisopropylaminoethyl)cyclopentane
1-Galla-1-(2-dibutylaminoethyl)cyclopentane
1-Galla-1-(3-diethylaminopropyl)cyclopentane
1-Galla-1-(3-dipropylaminopropyl)cyclopentane
1-Galla-1-(3-diisopropylaminopropyl)cyclopentane
1-Galla-1-(3-dibutylaminopropyl)cyclopentane
1-Galla-1-(4-dimethylaminobutyl)cyclopentane
1-Galla-1-(4-diethylaminobutyl)cyclopentane
1-Galla-1-(4-dipropylaminobutyl)cyclopentane
1-Galla-1-(4-isopropylaminobutyl)cyclopentane
1-Galla-1-(4-dibutylaminobutyl)cyclopentane
1-Galla-1-(3-dimethylaminopropyl)cyclohexane, b.p. 67° C./0.1 mbar
1-Galla-1-(3-diethylaminopropyl)cyclohexane, b.p. 94° C./0.01 mbar
1-Galla-1-(3-dipropylaminopropyl)cyclohexane
1-Galla-1-(3-diisopropylaminopropyl)cyclohexane
1-Galla-1-(3-dibutylaminopropyl)cyclohexane
1-Galla-1-(2-dimethylaminoethyl)cyclohexane
1-Galla-1-(2-diethylaminoethyl)cyclohexane
1-Galla-1-(2-dipropylaminoethyl)cyclohexane
1-Galla-1-(2-diisopropylaminoethyl)cyclohexane
1-Galla-1-(2-dibutylaminoethyl)cyclohexane
1-Galla-1-(4-dimethylaminobutyl)cyclohexane, b.p. 138° C./0.01 mbar
1-Galla-1-(4-diethylaminobutyl)cyclohexane
1-Galla-1-(4-dipropylaminobutyl)cyclohexane
1-Galla-1-(4-isopropylaminobutyl)cyclohexane
1-Galla-1-(4-dibutylaminobutyl)cyclohexane
1-Galla-1-(o-dimethylaminobenzyl)cyclobutane
1-Galla-1-(o-dimethylaminobenzyl)cyclopentane
1-Galla-1-(o-dimethylaminobenzyl)cyclohexane
1-Galla-1-(o-diethylaminobenzyl)cyclohexane
1-Galla-1-(o-dipropylaminobenzyl)cycloheptane
1-Inda-1-(2-diethylaminoethyl)cyclobutane
1-Inda-1-(2-dimethylaminoethyl)cyclopentane
1-Inda-1-(2-diethylaminoethyl)cyclopentane
1-Inda-1-(2-dipropylaminoethyl)cyclopentane
1-Inda-1-(2-diisopropylaminoethyl)cyclopentane
1-Inda-1-(2-dibutylaminoethyl)cyclopentane
1-Inda-1-(3-dimethylaminopropyl)cyclopentane
1-Inda-1-(3-diethylaminopropyl)cyclopentane
1-Inda-1-(3-dipropylaminopropyl)cyclopentane
1-Inda-1-(3-diisopropylaminopropyl)cyclopentane
1-Inda-1-(3-dibutylaminopropyl)cyclopentane
1-Inda-1-(4-dimethylaminobutyl)cyclopentane
1-Inda-1-(4-diethylaminobutyl)cyclopentane
1-Inda-1-(4-dipropylaminobutyl)cyclopentane
1-Inda-1-(4-diisopropylaminobutyl)cyclopentane
1-Inda-1-(4-dibutylaminobutyl)cyclopentane
1-Inda-1-(2-dimethylaminoethyl)cyclohexane,
1-Inda-1-(2-diethylaminoethyl)cyclohexane,
1-Inda-1-(2-dipropylaminoethyl)cyclohexane
1-Inda-1-(2-diisopropylaminoethyl)cyclohexane
1-Inda-1-(2-dibutylaminoethyl)cyclohexane
1-Inda-1-(3-dimethylaminopropyl)cyclohexane
1-Inda-1-(3-diethylaminopropyl)cyclohexane
1-Inda-1-(3-dipropylaminopropyl)cyclohexane
1-Inda-1-(3-diisopropylaminopropyl)cyclohexane
1-Inda-1-(3-dibutylaminopropyl)cyclohexane
1-Inda-1-(4-dimethylaminobutyl)cyclohexane,
1-Inda-1-(4-diethylaminobutyl)cyclohexane
1-Inda-1-(4-dipropylaminobutyl)cyclohexane
1-Inda-1-(4-diisopropylaminobutyl)cyclohexane
1-Inda-1-(4-dibutylaminobutyl)cyclohexane
1-Inda-1-(o-diisopropylaminobenzyl)cyclobutane
1-Inda-1-(o-dimethylaminobenzyl)cyclopentane
1-Inda-1-(o-dibutylaminobenzyl)cyclopentane
1-Inda-1-(o-dimethylaminobenzyl)cyclohexane
1-Inda-1-(o-diethylaminobenzyl)cyclohexane
1-Inda-1-(o-dimethylaminobenzyl)cyclooctane 2,5-Dimethyl-1-(3-dimethylaminopropyl)-2,5-diaza-1-aluminacyclopentane
2,5-Dimethyl-1-(3-dimethylaminopropyl)-2,5-diaza-1-aluminacyclohexane
2,5-Dimethyl-1-(3-dimethylaminopropyl)-2,5-diaza-1-aluminacycloheptane
2,5-Dimethyl-1-(3-dimethylaminopropyl)-2,5-diaza-1-aluminacyclopentane
2,5-Dimethyl-1-(3-diethylaminopropyl)-2,5-diaza-1-aluminacyclohexane
2,5-Dimethyl-1-(3-diethylaminopropyl)-2,5-diaza-1-aluminacycloheptane
2,5-Diethyl-1-(3-dimethylaminopropyl)-2,5-diaza-1-aluminacyclohexane
2,5-Diethyl-1-(3-dimethylaminopropyl)-2,5-diaza-1-aluminacyclopentane
2,5-Diethyl-1-(4-dimethylaminobutyl)-2,5-diaza-1-aluminacyclohexane
2,5-Diethyl-1-(4-dimethylaminobutyl)-2,5-diaza-1-aluminacyclopentane
2,5-Diethyl-1-(4-dimethylaminobutyl)-2,5-diaza-1-aluminacycloheptane
2-Ethyl-5-propyl-1-(4-dimethylaminobutyl)-2,5-diaza-1-aluminacyclohexane
2-Ethyl-5-propyl-1-(4-dimethylaminobutyl)-2,5-diaza-1-aluminacyclopentane
2-Ethyl-5-propyl-1-(4-dimethylaminobutyl)-2,5-diaza-1-aluminacycloheptane
2,5-Dimethyl-1-(3-dimethylaminopropyl)-2,5-diaza-1-gallacyclopentane, b.p. 220° C./0.1 mbar
2,5-Dimethyl-1-(3-dimethylaminopropyl)-2,5-diaza-1-gallacyclohexane
2,5-Dimethyl-1-(3-dimethylaminopropyl)-2,5-diaza-1-gallacycloheptane
2,5-Dimethyl-1-(3-diethylaminopropyl)-2,5-diaza-1-gallacyclopentane
2,5-Dimethyl-1-(3-diethylaminopropyl)-2,5-diaza-1-gallacyclohexane
2,5-Dimethyl-1-(3-diethylaminopropyl)-2,5-diaza-1-gallacycloheptane
2,5-Diethyl-1-(3-dimethylaminopropyl)-2,5-diaza-1-gallacyclohexane
2,5-Diethyl-1-(3-dimethylaminopropyl)-2,5-diaza-1-gallacyclopentane
2,5-Diethyl-1-(3-dimethylaminopropyl)-2,5-diaza-1-gallacycloheptane 2,5-Diethyl-1-(4-dimethylaminobutyl)-2,5-diaza-1-gallacyclohexane
2,5-Diethyl-1-(4-dimethylaminobutyl)-2,5-diaza-1-gallacyclopentane
2,5-Diethyl-1-(4-dimethylaminobutyl)-2,5-diaza-1-gallacycloheptane
2-Ethyl-5-propyl-1-(4-dimethylaminobutyl)-2,5-diaza-1-gallacyclohexane
2-Ethyl-5-propyl-1-(4-dimethylaminobutyl)-2,5-diaza-1-gallacyclopentane
2-Ethyl-5-propyl-1-(4-dimethylaminobutyl)-2,5-diaza-1-gallacycloheptane
2,5-Dimethyl-1-(3-dimethylaminopropyl)-2,5-diaza-1-indacyclopentane
2,5-Dimethyl-1-(3-dimethylaminopropyl)-2,5-diaza-1-indacyclohexane
2,5-Dimethyl-1-(3-dimethylaminopropyl)-2,5-diaza-1-indacycloheptane
2,5-Dimethyl-1-(3-diethylaminopropyl)-2,5-diaza-1-indacyclopentane
2,5-Dimethyl-1-(3-diethylaminopropyl)-2,5-diaza-1-indacyclohexane
2,5-Dimethyl-1-(3-diethylaminopropyl)-2,5-diaza-1-indacycloheptane
2,5-Diethyl-1-(3-dimethylaminopropyl)-2,5-diaza-1-indacyclohexane
2,5-Diethyl-1-(3-dimethylaminopropyl)-2,5-diaza-1-indacyclopentane
2,5-Diethyl-1-(3-dimethylaminopropyl)-2,5-diaza-1-indacycloheptane
2,5-Diethyl-1-(3-dimethylaminobutyl)-2,5-diaza-1-indacyclohexane
2,5-Diethyl-1-(3-dimethylaminobutyl)-2,5-diaza-1-indacyclopentane
2,5-Diethyl-1-(3-dimethylaminobutyl)-2,5-diaza-1-indacycloheptane
2-Ethyl-5-propyl-1-(4-dimethylaminobutyl)-2,5-diaza-1-indacyclohexane
2-Ethyl-5-propyl-1-(4-dimethylaminobutyl)-2,5-diaza-1-indacyclopentane
2-Ethyl-5-propyl-1-(4-dimethylaminobutyl)-2,5-diaza-1-indacycloheptane Typical examples of compounds of the formula II are:
5-Methyl-1-galla-5-azacyclooctane, m.p. −22° C.
1,5-Dimethyl-1-galla-5-azacyclooctane, b.p. 83° C./12 mbar
1,5-Diethyl-1-galla-5-azacyclooctane
1,5-Dipropyl-1-galla-5-azacyclooctane
1,5-Dimethyl-1-alumina-5-azacyclooctane, b.p. 76° C./4 mbar
1,5-Diethyl-1-alumina-5-azacyclooctane, b.p. 71° C./0.6 mbar
1,5-Diisopropyl-1-alumina-5-azacyclooctane
1,5-Dibutyl-1-alumina-5-azacyclooctane
1-Methyl-5-ethyl-1-galla-5-azacyclooctane
1-Ethyl-5-methyl-1-alumina-5-azacyclooctane, b.p. 71° C./0.6 mbar
1,6-Dimethyl-1-galla-6-azacyclodecane
1,6-Dimethyl-1-alumina-6-azacyclodecane
1,6-Diethyl-1-galla-6-azacyclodecane
1,4-Dimethyl-1-galla-4-azacyclohexane
1,6-Diethyl-1-alumina-6-azacyclodecane
1-Galla-5-azabicyclo[3.3.3]undecane, m.p. 54° C.
1-Galla-4-azabicyclo[2.2.2]octane,
1-Alumina-5-azabicyclo[3.3.3]undecane, b.p. 80° C./0.4 mbar
1-Alumina-4-azabicyclo[2.2.2]octane
1-Galla-6-azabicyclo[4.4.4]tetradecane
1-Alumina-6-azabicyclo[4.4.4]tetradecane
1,5-Dimethyl-1-inda-5-azacyclooctane, b.p. 38° C./0.05mbar
1,5-Diethyl-1-inda-5-azacyclooctane
1,5-Dipropyl-1-inda-5-azacyclooctane
1,5-Diisopropyl-1-inda-5-azacyclooctane
1,5-Dibutyl-1-inda-5-azacyclooctane
1-Methyl-5-ethyl-1-inda-5-azacyclooctane
1-Ethyl-5-propyl-1-inda-5-azacyclooctane
1,6-Dimethyl-1-inda-6-azacyclodecane
1,6-Diethyl-1-inda-6-azacyclodecane
1,4-Dimethyl-1-inda-4-azacyclohexane
1-Inda-5-azabicyclo[3.3.3]undecane
1-Inda-4-azabicyclo[2.2.2]octane
1-Methyl-5-cyclohexyl-1-inda-5-azacyclooctane
1-Methyl-5-phenyl-1-inda-5-azacyclooctane
1-Inda-6-azabicyclo[4.4.4]tetradecane
1,6-Dimethyl-1-galla-6-azacyclodecane
1,6-Diethyl-1-galla-6-azacyclodecane
1,6-Dipropyl-1-galla-6-azacyclodecane
1,6-Diisopropyl-1-galla-6-azacyclodecane
1,6-Dibutyl-1-galla-6-azacyclodecane
1,6-Di-tert-butyl-1-galla-6-azacyclodecane
1,6-Diisobutyl-1-galla-6-azacyclodecane
1,4-Dimethyl-1-galla-4-azacyclohexane
1,4-Diethyl-1-galla-4-azacyclohexane
1,4-Dipropyl-1-galla-4-azacyclohexane
1,4-Diisopropyl-1-galla-4-azacyclohexane
1,4-Dibutyl-1-galla-4-azacyclohexane
1,4-Diisobutyl-1-galla-4-azacyclohexane
1,4-Di-tert-butyl-1-galla-4-azacyclohexane
1-Methyl-5-ethyl-1-galla-5-azacyclooctane
1-Methyl-5-propyl-1-galla-5-azacyclooctane
1-Propyl-5-methyl-1-galla-5-azacyclooctane, b.p. 86° C./0.01 mbar
1-Ethyl-5-methyl-1-galla-5-azacyclooctane, b.p. 64° C./1 mbar
1-Ethyl-6-propyl-1-galla-6-azacyclodecane
1-Propyl-6-butyl-1-galla-6-azacyclodecane
1-Methyl-6-ethyl-1-galla-6-azacyclodecane
1-Methyl-4-ethyl-1-galla-4-azacyclohexane
1-Propyl-4-methyl-1-galla-4-azacyclohexane
1-Ethyl-4-butyl-1-galla-4-azacyclohexane Preference is given to organoaluminum compounds of the formulae I and II.

Particularly preferred are the compounds 1-alumina-1-(3-dimethylaminopropyl)cyclohexane and 1,5-dimethyl-1-alumina-5-azacyclooctane.

Most of the cyclic organometallic compounds of the formulae I and II are as such already known per se. Thus, compounds of the formula I have been described for the first time in DE 3817090 and in DE 4009394 and compounds of the formula II have been described for the first in DE 3726485. It can already be seen from the specified documents that the compounds are stable towards air and moisture.

However, they are only proposed for use in the production of thin metal or compound semiconductor layers by gas phase deposition. These documents make no reference to the suitability of these compounds as activating components in coordination catalyst systems for olefin polymerization or metathesis.

The compounds of the formulae I and II are prepared by methods known per se, as described in the literature (e.g. G. Bähr, P. Burba, Methoden der Organischen Chemie, Vol. XIII/4, Georg Thieme Verlag, Stuttgart (1970)), namely under reaction conditions which are known and suitable for the specified reactions. For this purpose, use can also be made of variants known per se and not mentioned here.

Thus these compounds can be prepared, for example, by reacting alkylmetal chlorides with an alkali metal organocompound of the corresponding Lewis base or a Grignard compound in an inert solvent.

Further details of the synthesis of these compounds can be taken from the abovementioned patent documents or Chem. Bet. 124, 1113–1119 (1991).

Coordination catalyst systems which contain the cyclic organometallic compounds of the formulae I and II of the invention are particularly suitable for the polymerization of 1-alkenes and 1-alkynes, with it being possible to obtain both homopolymers from uniform monomers and copolymers from monomer mixtures. They are furthermore suitable for the metathesis of 1-alkenes and 1-alkynes and for the ring-opening metathesis of cyclic alkenes.

In the use according to the invention of the compounds of the formulae I and II as activating components in coordination catalyst systems, it has surprisingly been found that as a result the catalyst systems are less sensitive to (atmospheric) oxygen and moisture, so that it is not necessary to take such strict protective measures as are required for coordination catalysts activated with conventional aluminum alkyls. This finding is particularly surprising and not foreseeable, especially since the use of structurally similar, but non-cyclic organoaluminum compounds, such as, for example, (3-diethylaminopropyl)di-isobutylaluminum, is already known in certain coordination catalyst systems. U.S. Pat. No. 3,154,528 discloses coordination catalyst systems based on vanadium tetrachloride and activated with such non-cyclic compounds, which catalyst systems are, however, described as being just as air and moisture sensitive as the conventional coordination catalyst systems. JP 60-240706, JP 61-007305, JP 61-252205, JP 62-100505 and JP 62-138506 disclose coordination catalyst systems based on titanium compounds, which likewise contain such non-cyclic organoaluminum compounds and also further compounds functioning as electron donors, which, however, are first activated with conventional aluminum alkyls. Owing to the presence of the latter, these catalyst systems are likewise extremely sensitive and require the usual strict protective measures.

Our own investigations using these known non-cyclic organoaluminum compounds in Ziegler-Natta and Phillips catalyst systems also confirm that these definitely require activation with conventional aluminum alkyls to obtain an olefin polymer at all or at least usable product yields.

In the coordination catalyst systems of the invention, an additional activation by aluminum alkyls or other activators is not required.

In the coordination catalyst systems of the invention, moderate exposure to air, oxygen or moisture does not result in destruction or a drastic reduction in activity. Correspondingly coordination catalyst systems based on supported chromium do not glow, for example, in air, but continue to be as usable as before. This has the very advantageous consequence that the handling of the coordination catalyst systems of the invention is substantially less problematical in preparation, storage and use. The complicated exclusion of even traces of air, oxygen and moisture from the solvents, monomers and protective gases used in the polymerization can therefore be omitted.

In addition, the compounds of the formulae I and II to be used according to the invention in coordination catalyst systems give further advantageous results in the intended use in polymerization processes and metathesis reactions.

Thus, the corresponding coordination catalyst systems according to the invention generally show an extremely high activity. This has the consequence that more product is formed with the amount of catalyst used or the required amount of catalyst can be correspondingly reduced. Advantageous consequences of this are that correspondingly less catalyst has to be separated off from the product or products having a lower residual catalyst content are obtained and, not least, the costs are also reduced because of lower catalyst consumption. Naturally, numerous further factors also have an influence here, such as the qualitative and quantitative composition of the catalyst systems, the nature of the monomers or the composition of monomer mixtures used in copolymerization, reaction conditions and operating procedure in the polymerization. However, those skilled in the art can easily determine and optimize the most suitable catalyst system for their purposes with the aid of routine experiments. Thus, for example, a Ziegler-Natta catalyst system based on $Ti/MgCl_2$ which had been activated with the compound 1-alumina-1-(3-dimethylaminopropyl)cyclohexane as cocatalyst showed an optimum in respect of constant activity and product yield in the polymerization of ethylene on an industrial scale when the molar ratio of Ti to Al in the catalyst system was in the range 1:40–50.

Furthermore, for the coordination catalyst systems of the invention in olefin polymerization, there is found a pronounced specificity in the direction of high molecular weights and narrow molecular weight distributions. These findings too are dependent on factors such as the composition of the catalyst system, the nature of the monomers and process conditions used, but can easily be optimized for the particular application. Thus, for example, in the polymerization of 1-octene and 1-decene using Phillips catalyst systems based on $Cr/SiO_2$ which had been activated with 1-alumina-1-(3-dimethylaminopropyl)cyclohexane as cocatalyst, with variation of the molar ratio of Cr to Al in the range from 1:0.5 to 1:4, high product yields and high molecular weights were obtained throughout and for 1-octene there was an optimum in respect of a narrow molecular weight distribution at a ratio of Cr to Al of 1:1.

A further advantageous finding which has emerged is that Phillips catalysts activated with compounds of the formulae I and II do not, as is otherwise usual, stick together with the polymer and remain adhering to the reaction apparatus, which makes the removal and separation considerably easier.

Metathesis catalysts based on $Mo/SiO_2$ activated with 1-alumina-1-(3-dimethylaminopropyl)cyclohexane show a surprisingly high product specificity. Thus, for example, the metathesis of 1-octene using the specified catalyst system gave exclusively the desired $C_4$-alkene, while a catalyst system of this type activated with triisobutylaluminum gave, besides the desired product, a high proportion of byproduct in the form of a $C_2$- to $C_{20}$-alkene mixture.

In the polymerization of 1-alkenes, the catalysts of the invention can, if the situation arises, act in a pronounced stereoselective way to give isotactic polymers. In metathesis or ring-opening metathesispolymerization, particular stereoisomers or products having a particular configuration can be preferentially formed. This stereoselectivity can be additionally influenced by targeted structuring of the compounds of the formula I and II, in particular on their cyclic structural elements. If, for example, in formula I it is the case that $X^1$ and/or $X^2$ are $CHR^1$, the radical $R^1$ not being hydrogen, then the cyclic structural element has an asymmetric carbon atom and thus a center of chirality which can effect stereoselective induction in polymerization or metathesis of 1-alkenes. Such a stereoselective or optionally enantioselective induction by a corresponding catalyst system is preferably to be expected when the compounds of the formula I are used in enantiomerically or diastereomerically pure form.

The Ziegler-Natta and the Phillips polymerization of ethylene and propylene is successful without problems using the coordination catalyst systems of the invention even under mild conditions, such as, for example, at about 70° C. and under a pressure of 8-10 bar. In comparison with activation using conventional aluminum alkyls, such as, for example, triisobutylaluminum, this achieves predominantly higher product yields and, in particular, significantly higher molecular weights. Olefin polymers having a particularly high molecular weight, for example above $10^6$, as are easily obtainable on a laboratory scale and without technical optimization using the catalyst systems of the invention, are of great industrial importance.

Coordination catalyst systems of the "Ziegler-Natta" type and of the "Phillips" type which are activated with the compounds of the formulae I and II of the invention as cocatalysts additionally show the surprising property that they can also be used to polymerize polar olefinically unsaturated monomers. It is known that conventional catalyst systems essentially allow only 1-alkenes and 1-alkynes to be polymerized. Styrene, for example, hardly undergoes coordination polymerization and even more polar monomers such as vinyl compounds and acrylic acid derivatives do not undergo coordination polymerization at all. Presumably this is because these polar compounds deactivate the metal atoms of the primary catalyst and/or cocatalyst by means of a strong coordinate bond. However, as a result of the intramolecular coordinate saturation, this is no longer possible in the compounds of the formulae I and II, which explains the notable activity of the catalyst systems of the invention towards polar monomers.

The use according to the invention of the compounds of the formulae I and II as activating components in coordination catalyst systems is carried out completely analogously to and in substitution of the hitherto customary organometallics and, in particular, the extremely sensitive and dangerous aluminum alkyls. Owing to the increased activity, both the proportion of organometallic compound in the catalyst system and the amount of catalyst in the reaction can be reduced. The preparation and use of the catalysts is carried out in a manner known per se as is customary for the particular system and the particular use. In general, olefin polymerization and metathesis are carried out using heterogeneous catalysis in the suspension process. For this purpose, the supported pre-catalyst is first prepared from the catalytically active transition metal compound and a finely divided support material, this precatalyst is, if required, activated or preactivated in a conventional manner and then suspended in a solvent, for example in an alkane hydrocarbon such as pentane or hexane. The addition of the cocatalyst is carried out, as is also customary otherwise, directly prior to the reaction of the monomers or "in situ" in the presence of the same. The control of the reaction and also the isolation and workup of the reaction products is likewise carried out in a completely analogous way. As already mentioned, owing to the stability of the compounds of the formulae I and II and the lower sensitivity of the resulting catalyst systems, all these procedures can be carried out with substantially fewer problems and with substantially fewer strict protective and safety measures.

The invention thus makes accessible novel coordination catalyst systems having advantageous properties and also a considerably expanded breadth of use, which catalyst systems can additionally be tailored to the respective requirements of the application.

In the following examples, all handling, if not otherwise indicated, is carried out under a protective gas atmosphere ($N_2$, Ar) and with-exclusion of moisture.

EXAMPLE 1

0.25 mol of magnesium turnings, activated by iodine, are initially charged in 100 ml of diethyl ether. After addition of 0.06 mol of 1,5-dibromopentane at room temperature, the mixture is heated for 3 hours under reflux.

The Grignard solution decanted off from the magnesium and 0.06 mol of 3-dimethylaminopropylaluminum dichloride, dissolved in 150 ml of ether, are synchronously combined and reacted with vigorous stirring.

Subsequently the reaction mixture is stirred at room temperature. The volatile constituents are distilled off at a bath temperature of up to 180° C. and a pressure of 10-2 mbar and again fractionally distilled.

1-Alumina-1-(3-dimethylaminopropyl)cyclohexane is obtained as a water-white, air-stable liquid having a boiling point of 98°/0.6 mbar.

EXAMPLE 2

2.9 g (119 mmol) of magnesium grit are initially charged in 100 ml of THF and heated under reflux. 10 g (54 mmol) of methylbis(3,3'-chloropropyl)amine, dissolved in 40 ml of THF, are added. Subsequently the mixture is heated for a further 2 hours under reflux.

At room temperature, 5.7 g (50 mmol) of methylaluminum dichloride in 20 ml of THF are added to the Grignard solution. The mixture is stirred for 24 hours at room temperature and then heated for 3 hours under reflux. The solution is decanted off from the precipitated $MgCl_2$ and, after drawing off the solvent, 1,5-dimethyl-1-alumina-5-azacyclooctane is obtained by vacuum distillation as a clear, stable liquid having a boiling point of 71°/0.6 mbar.

EXAMPLE 3

3.6 g (148 mmol) of magnesium grit are initially charged in 100 ml of THF and heated under reflux. 12 g (49 mmol) of 3-chloro-N,N-bis(3-chloropropyl)propan-1-amine in 40 ml of THF are added, and the mixture is heated for a further 2 hours.

At room temperature, 6.6 g (47 mmol) of aluminum trichloride in 20 ml of THF, are added to the Grignard solution. The mixture is stirred for 24 hours at room temperature and is then heated for 4 hours under reflux. After distilling off the solvent and purification by vacuum distillation, 1-alumina-5-azabicyclo[3.3.3]undecane is obtained as a clear, stable liquid having a boiling point of 80°/0.4 mbar.

EXAMPLE 4

Supported Cr(VI) pre-catalyst 1,000 g of silica gel (particle size 200-500 mm) are boiled for 45 minutes in 3,000 ml of distilled $H_2O$, washed three times with hot $H_2O$ and dried for 15 hours at 115° C./75 mbar. This material is subsequently slurried in a solution of 46 g of $CrO_3$ in 200 ml of water, stirred for 30 minutes, filtered off and dried at 70° C./75 mbar for 12 hours and then for 2 hours at 115/75 mbar. The product is then heated in a stream of oxygen (fluidized bed or rotary tube) to 800° C. over the course of 6 hours and left at this temperature for 1 hour. After cooling to 350° C., the oxygen is replaced by argon. The catalyst contains about 1% of Cr(VI).

EXAMPLE 5

Supported Cr(II) pre-catalyst

First, the procedure of Example 5 is repeated. However, argon is then displaced by CO; the reduction is carried out in the CO stream at 350° C./60 min. Finally, the CO is again replaced by argon and the material is cooled to room temperature. The catalyst contains about 0.84% of Cr(II).

EXAMPLE 6

Supported Mo(VI) pre-catalyst 1.67 mmol of $MoO_2$-acetylacetonate complex are dissolved in 30 ml of $CH_2Cl_2$ and applied to 9 g of silica gel (particle size 200–500 mm). Subsequently the material is washed with $CH_2Cl_2$ and dried at −10° C. in a high vacuum.

EXAMPLE 7

Polymerization of 1-octene over Cr(VI)

In parallel batches, the pre-catalyst of Example 4 is suspended in n-pentane and admixed with differing amounts of the compound of Example 1 as cocatalyst. Subsequently, 1-octene is added in the ratio Cr:1-octene of 1:100 and the mixture is shaken for 24 hours at 20° C. The catalyst is filtered off and washed with n-pentane. The pentane eluates are evaporated. The polymer product is analyzed by IR and $^{13}$C-NMR spectroscopy and by gel permeation chromatography (polystyrene standard). Table 1 shows the results.

TABLE 1

| Cr:Al | Yield in % | $M_w$ | $D = M_w/M_n$ |
|---|---|---|---|
| 1:0.5 | 55 | 10,900 | 8.45 |
| 1:1 | 86 | 21,900 | 6.35 |
| 1:1.5 | 67 | 15,650 | 9.1 |
| 1:2 | 43 | 14,900 | 8.4 |

Throughout, high molecular weights ($M_w$) with narrow molecular weight distributions ($D=M_w/M_n$) were obtained together with good yields. The catalyst having Cr:Al=1:1 gave optimum results.

EXAMPLE 8

Polymerization of 1-octene over Cr(II)

The procedure of Example 7 is repeated using the pre-catalyst of Example 5. Table 2 shows the results.

TABLE 2

| Cr:Al | Yield in % | $M_w$ | $D = M_w/M_n$ |
|---|---|---|---|
| 1:1 | 91 | 37,900 | 2.1 |
| 1:2 | 77 | 62,800 | 11.0 |
| 1:4 | 68 | 78,700 | 7.9 |
| Comparative experiment using triethylaluminum as cocatalyst | | | |
| 1:2.7 | 52 | 31,800 | broad/bimodal |

EXAMPLE 9

Polymerization of 1-decene over Cr(II)

The procedure of Example 8 is repeated using 1-decene. Table 3 shows the results.

TABLE 3

| Cr:Al | Yield in % | $M_w$ | $D = M_w/M_n$ |
|---|---|---|---|
| 1:2 | 83 | 47,200 | 9.8 |
| 1:3 | 97 | 77,700 | 11.6 |
| 1:4 | 85 | 53,200 | 14.5 |

EXAMPLE 10

Metathesis of 1-octene over Mo(VI)

In parallel batches, 300 mg in each case of the pre-catalyst of Example 6 (corresponding to 0.05 mmol of Mo) are admixed with 1-octene in a ratio Mo:1-octene of 1:2,500 and differing amounts of the compound of Example 1 are added as cocatalyst. The mixture is allowed to react for 24 hours at 122° C. The conversion of 1-octene and the tetradecene ($C_{14}$) formed and any byproducts are determined by gas chromatography.

In an analogous comparative experiment, triisobutylaluminum (TIBA) is used as cocatalyst. Table 4 shows the results.

TABLE 4

| Mo:Al | Yield in % Product $C_{14}$ | Yield in % Byproducts $C_2$–$C_{20}$ |
|---|---|---|
| 1:2 | 14.8 | — |
| 1:4 | 19.4 | — |
| 1:10 | 4.8 | — |
| Comparative experiment using TIBA | | |
| 1:4 | 12.3 | 16.2 |

EXAMPLE 11

Polymerization of 1-octene over Cr(II) with and without admission of oxygen

The procedure of Example 8 is repeated. In a parallel batch, 5 ml of $O_2$ gas is injected by means of a syringe prior to the addition of the alkene. Table 5 shows the results.

TABLE 5

| Cr:Al | Yield in % | $M_w$ | $D = M_w/M_n$ |
|---|---|---|---|
| Addition of $O_2$ | | | |
| 1:3 | 73 | 76,500 | 13.4 |
| No addition of $O_2$ | | | |
| 1:3 | 87 | 78,700 | 7.9 |

The result verifies that the addition of $O_2$ exercises no substantial influence on the activity of the catalyst system.

EXAMPLE 12

Polymerization of ethylene over Cr(VI)

In parallel batches, 200 mg in each case of pre-catalyst of Example 4 are suspended in n-heptane in an autoclave. To this are added differing amounts of the compound of Example 1 or, for comparison, of cocatalysts of the prior art, and at a temperature of 70° C. ethylene is then fed in under a pressure of 10 bar. After 24 hours the mixture is worked up in the usual way. Table 6 shows the results.

TABLE 6

| Cr:Al | Yield g polymer/g Cr · h | m.p. °C. | $M_w$ | Appearance |
|---|---|---|---|---|
| 1:0 | 0 | — | — | no polymer |
| 1:1 | 1,700 | 189–192 | $1.02 \cdot 10^6$ | white, finely particulate polymer |
| 1:5 | 1,250 | 175–200 | $1.03 \cdot 10^6$ | white, finely particulate polymer |
| 1:10 | 1,300 | 188–194 | $1.2 \cdot 10^6$ | white, finely particulate polymer |
| 1:15 | 1,400 | 191–195 | $1.1 \cdot 10^6$ | white, finely particulate polymer |
| Comparative experiments using TIBA | | | | |
| 1:1 | 1,200 | 185–188 | $8.5 \cdot 10^5$ | white, finely particulate polymer |
| 1:15 | 1,500 | 174–177 | $5.9 \cdot 10^5$ | white, finely particulate polymer |
| Comparative experiment using (2-dimethylaminoethoxy)dimethylaluminum | | | | |
| 1:25 | 0 | — | — | no polymer |

The cocatalyst of the invention effects excellent yields and, in comparison with TIBA, an increase in the molecular weight. The non-cyclic compound effects no polymerization.

EXAMPLE 13

Ziegler-Natta polymerization of ethylene

In parallel batches, 50 mg in each case of $TiCl_4$ are suspended in n-heptane in an autoclave and differing amounts of the compound of Example 1 or, for comparison, of cocatalysts of the prior art are added. At a temperature of 70° C., ethylene is then fed in under a pressure of 8–10 bar and the reaction is stopped after one hour. Table 7 shows the results.

TABLE 7

| Ti:Al | Yield g polymer/g Ti · h | m.p. °C. | $M_w$ | Appearance |
|---|---|---|---|---|
| 1:3 | 14,700 | 175–210 | $7.9 \cdot 10^6$ | finely particulate, white |
| 1:5 | 15,400 | 190 (decomposition) | $2 \cdot 10^6$ | finely particulate, white |
| Comparative experiment using TIBA | | | | |
| 1:3 | 18,600 | 196–205 | $3.4 \cdot 10^5$ | coarsely particulate, gray |
| Comparative experiment using (3 dimethylaminopropyl)diisopropylaluminum | | | | |
| 1:5 | 0 | — | — | no polymer |
| Comparative experiment using (2-dimethylaminoethoxy)dimethylaluminum | | | | |
| 1:5 | — | — | — | traces of polymer |

The cocatalyst of the invention effects excellent yields and, in comparison with TIBA, an increase in the molecular weight. The non-cyclic compounds effect no polymerization or only traces of polymerization.

EXAMPLE 14

Industrial Ziegler-Natta polymerization of ethylene

The polymerization of ethylene is carried out by the suspension process in n-heptane at a constant ethylene partial pressure of 1 bar, a temperature of 80° C. and a stirring speed of 1,500 rpm in the presence of an industrial Ziegler-Natta catalyst based on $Ti/MgCl_2$ having a 1% Ti content and the compound of Example 1 as cocatalyst.

At a ratio Ti:Al of 1:40–1:50, the catalyst system has a constant activity of 30–50 kg polyethylene/g Ti.h.bar $C_2H_4$.

We claim:

1. A process for preparing unsaturated hydrocarbon compounds by a catalyzed metathesis reaction of alkenes or alkynes, comprising subjecting to conditions effective for metathesis alkenes or alkynes in the presence of a metathesis catalyst which is a coordination catalyst system, based on a transition metal compound of subgroup IV to VIII and a cyclic organometallic compound of main group III of the periodic table of elements, wherein said cyclic organometallic compound is a compound of the formulae I or II

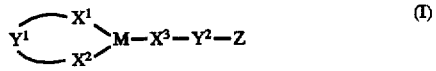  (I)

in which

M is B, Al, Ga, In, $X^1, X^2, X^3$ are, in each case independently of one another, $CHR^1, NR^2, O, S,$ $Y^1, Y^2$ are, in each case independently of one another, $—(CH_2)_m—$, $o-(CH_2)_p—C_6H_4—(CH_2)_q$, $o-(CH_2)_p—C_6H_6—(CH_2)_q$, $o-(CH_2)_q—C_6H_8—(CH_2)_q$, $o-(CH_2)_p—C_6H_{10}—(CH_2)_q$, $o-(CH_2)_p—C_5H_4—(CH_2)_q$, $o-(CH_2)_p—C_5H_6—(CH_2)_q$, $o-(CH_2)_p—C_5H_8—(CH_2)_q$, $—(CH_2)_p—CH=CH=(CH_2)_q$ Z is $NR^3R^4$, $PR^3R^4$, $OR^5$, $SR^5$ $R^1$ is H, OH, halogen, $C_{1-6}$-alkyl or $C_{1-6}$-alkoxy, $C_{5-7}$-cycloalkyl, phenyl, $R^2, R^3, R^4, R^5$ are, in each case independently of one another, H or $C_{1-6}$-alkyl, $C_{5-7}$-cycloalkyl, phenyl, $R^3$ and $R^4$ together also a $C_{4-6}$-alkylene bridge, m m is a number from 1 to 6, p, q are, in each case independently of one another, a number from 0 to 2,

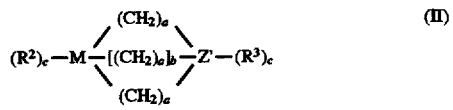  (II)

having M, $R^2$ and $R^3$ as defined above and in which

Z' is N, P, a is a number from 2 to 4, b, c are the number 0 or 1 with b+c=1.

2. A process according to claim 1, wherein in the coordination catalyst system $X^3$ is $—CH_2—$, $—O—$, $—S—$ or an amino group optionally substituted by $C_{1-6}$-alkyl, $C_{5-7}$-cycloalkyl or phenyl.

3. A process according to claim 1, wherein in the coordination catalyst system $Y^2$ is $—(CH_2)_m—$ and m is 1–6.

4. A process according to claim 1, wherein in the coordination catalyst system $Y^2$ is $—(CH_2)_p-CH=CH=(CH_2)_q—$, in which the double bond has a cis configuration.

5. A process according to claim 1, wherein in the coordination catalyst system in formula II, b is zero, and $R^2$ and $R^3$ are each independently H, $C_{1-6}$-alkyl, $C_{5-7}$-cycloalkyl or phenyl.

6. A process according to claim 1, wherein in the coordination catalyst system the compound of formula I is
1-Alumina-1-(4-dimethylaminobutyl)cyclobutane,
1-Alumina-1-(2-dimethylaminoethyl)cyclopentane,
1-Alumina-1-(2-diethylaminoethyl)cyclopentane,
1-Alumina-1-(2-dipropylaminoethyl)cyclopentane,
1-Alumina-1-(2-diisopropylaminoethyl)cyclopentane,
1-Alumina-1-(2-dibutylaminoethyl)cyclopentane,
1-Alumina-1-(3-dimethylaminopropyl)cyclopentane,
1-Alumina-1-(3-diethylaminopropyl)cyclopentane,
1-Alumina-1-(3-dipropylaminopropyl)cyclopentane,
1-Alumina-1-(3-diisopropylaminopropyl)cyclopentane,
1-Alumina-1-(3-dibutylaminopropyl)cyclopentane,
1-Alumina-1-(4-dimethylaminobutyl)cyclopentane,
1-Alumina-1-(4-diethylaminobutyl)cyclopentane,
1-Alumina-1-(4-dipropylaminobutyl)cyclopentane,
1-Alumina-1-(4-diisopropylaminobutyl)cyclopentane,
1-Alumina-1-(4-dibutylaminobutyl)cyclopentane,
1-Alumina-1-(3-dimetylaminopropyl)-2-methylcyclopentane,
1-Alumina-1-(2-dimethylaminoethyl)cyclohexane,
1-Alumina-1-(2-diethylaminoethyl)cyclohexane,
1-Alumina-1-(2-dipropylaminoethyl)cyclohexane,
1-Alumina-1-(2-diisopropylaminoethyl)cyclohexane,
1-Alumina-1-(2-dibutylaminoethyl)cyclohexane,
1-Alumina-1-(3-dimethylaminopropyl)cyclohexane,
1-Alumina-1-(3-diethylaminopropyl)cyclohexane,
1-Alumina-1-(3-dipropylaminopropyl)cyclohexane,
1-Alumina-1-(3-diisopropylaminopropyl)cyclohexane,
1-Alumina-1-(3-dibutylaminopropyl)cyclohexane,
1-Alumina-1-(4-dimethylaminobutyl)cyclohexane,
1-Alumina-1-(4-diethylaminobutyl)cyclohexane,
1-Alumina-1-(4-dipropylaminobutyl)cyclohexane,
1-Alumina-1-(4-diisopropylaminobutyl)cyclohexane,
1-Alumina-1-(4-dibutylaminobutyl)cyclohexane,
1-Alumina-1-(o-diethylaminobenzyl)cyclopentane,
1-Alumina-1-(o-diethylaminobenzyl)cyclohexane,
1-Alumina-1-(o-diisopropylaminobenzyl)cyclohexane,
1-Alumina-1-(3-dimethylaminopropyl)-2-methylcyclohexane,
1-Alumina-1-(2-o-dimethylaminophenylethyl)cyclopentane,
1-Alumina-1-(2-o-diethylaminophenylethyl)cyclobutane,
1-Galla-1-(3-dimethylaminopropyl)cyclobutane,
1-Galla-1-(2-dimethylaminoethyl)cyclopentane,
1-Galla-1-(3-dimethylaminopropyl)cyclopentane,
1-Galla-1-(2-dimethylaminoethyl)cyclopentane,
1-Galla-1-(2-diethylaminoethyl)cyclopentane,
1-Galla-1-(2-dipropylaminoethyl)cyclopentane,
1-Galla-1-(2-diisopropylaminoethyl)cyclopentane,
1-Galla-1-(2-dibutylaminoethyl)cyclopentane,
1-Galla-1-(3-diethylaminopropyl)cyclopentane,
1-Galla-1-(3-dipropylaminopropyl)cyclopentane,
1-Galla-1-(3-diisopropylaminopropyl)cyclopentane,
1-Galla-1-(3-dibutylaminopropyl)cyclopentane,
1-Galla-1-(4-dimethylaminobutyl)cyclopentane,
1-Galla-1-(4-diethylaminobutyl)cyclopentane,
1-Galla-1-(4-dipropylaminobutyl)cyclopentane,
1-Galla-1-(4-isopropylaminobutyl)cyclopentane,
1-Galla-1-(4-dibutylaminobutyl)cyclopentane,
1-Galla-1-(3-dimethylaminopropyl)cyclohexane,
1-Galla-1-(3-diethylaminopropyl)cyclohexane,
1-Galla-1-(3-dipropylaminopropyl)cyclohexane,
1-Galla-1-(3-diisopropylaminopropyl)cyclohexane,
1-Galla-1-(3-dibutylaminopropyl)cyclohexane,
1-Galla-1-(2-dimethylaminoethyl)cyclohexane,
1-Galla-1-(2-diethylaminoethyl)cyclohexane,
1-Galla-1-(2-dipropylaminoethyl)cyclohexane,
1-Galla-1-(2-diisopropylaminoethyl)cyclohexane,
1-Galla-1-(2-dibutylaminoethyl)cyclohexane,
1-Galla-1-(4-dimethylaminobutyl)cyclohexane,
1-Galla-1-(4-diethylaminobutyl)cyclohexane,
1-Galla-1-(4-dipropylaminobutyl)cyclohexane,
1-Galla-1-(4-isopropylaminobutyl)cyclohexane,
1-Galla-1-(4-dibutylaminobutyl)cyclohexane,
1-Galla-1-(o-dimethylaminobenzyl)cyclobutane,
1-Galla-1-(o-dimethylaminobenzyl)cyclopentane,
1-Galla-1-(o-dimethylaminobenzyl)cyclohexane,
1-Galla-1-(o-diethylaminobenzyl)cyclohexane,
1-Galla-1-(o-dipropylaminobenzyl)cycloheptane,
1-Inda-1-(2-diethylaminoethyl)cyclobutane,
1-Inda-1-(2-dimethylaminoethyl)cyclopentane,
1-Inda-1-(2-diethylaminoethyl)cyclopentane,
1-Inda-1-(2-dipropylaminoethyl)cyclopentane,
1-Inda-1-(2-diisopropylaminoethyl)cyclopentane,
1-Inda-1-(2-dibutylaminoethyl)cyclopentane,
1-Inda-1-(3-dimethylaminopropyl)cyclopentane,
1-Inda-1-(3-diethylaminopropyl)cyclopentane,
1-Inda-1-(3-dipropylaminopropyl)cyclopentane,
1-Inda-1-(3-diisopropylaminopropyl)cyclopentane,
1-Inda-1-(3-dibutylaminopropyl)cyclopentane,
1-Inda-1-(4-dimethylaminobutyl)cyclopentane,
1-Inda-1-(4-diethylaminobutyl)cyclopentane,
1-Inda-1-(4-dipropylaminobutyl)cyclopentane,
1-Inda-1-(4-diisopropylaminobutyl)cyclopentane,
1-Inda-1-(4-dibutylaminobutyl)cyclopentane,
1-Inda-1-(2-dimethylaminoethyl)cyclohexane,
1-Inda-1-(2-diethylaminoethyl)cyclohexane,
1-Inda-1-(2-dipropylaminoethyl)cyclohexane,
1-Inda-1-(2-diisopropylaminoethyl)cyclohexane,
1-Inda-1-(2-dibutylaminoethyl)cyclohexane,
1-Inda-1-(3-dimethylaminopropyl)cyclohexane,
1-Inda-1-(3-diethylaminopropyl)cyclohexane,
1-Inda-1-(3-dipropylaminopropyl)cyclohexane,
1-Inda-1-(3-diisopropylaminopropyl)cyclohexane,
1-Inda-1-(3-dibutylaminopropyl)cyclohexane,
1-Inda-1-(4-dimethylaminobutyl)cyclohexane,
1-Inda-1-(4-diethylaminobutyl)cyclohexane,
1-Inda-1-(4-dipropylaminobutyl)cyclohexane,
1-Inda-1-(4-diisopropylaminobutyl)cyclohexane,
1-Inda-1-(4-dibutylaminobutyl)cyclohexane,
1-Inda-1-(o-diisopropylaminobenzyl)cyclobutane,
1-Inda-1-(o-dimethylaminobenzyl)cyclopentane,
1-Inda-1-(o-dibutylaminobenzyl)cyclopentane,
1-Inda-1-(o-dimethylaminobenzyl)cyclohexane,
1-Inda-1-(o-diethylaminobenzyl)cyclohexane,
1-Inda-1-(o-dimethylaminobenzyl)cyclooctane,
2,5-Dimethyl-1-(3-dimethylaminopropyl)-2,5-diaza-1-aluminacyclopentane,
2,5-Dimethyl-1-(3-dimethylaminopropyl)-2,5-diaza-1-aluminacyclohexane,
2,5-Dimethyl-1-(3-dimethylaminopropyl)-2,5-diaza-1-aluminacycloheptane,
2,5-Dimethyl-1-(3-dimethylaminopropyl)-2,5-diaza-1-aluminacyclopentane,
2,5-Dimethyl-1-(3-dimethylaminopropyl)-2,5-diaza-1-aluminacyclohexane,
2,5-Dimethyl-1-(3-dimethylaminopropyl)-2,5-diaza-1-aluminacycloheptane,
2,5-Dimethyl-1-(3-dimethylaminopropyl)-2,5-diaza-1-aluminacyclohexane, 2,5-Dimethyl-1-(3-dimethylaminopropyl)-2,5-diaza-1-aluminacyclopentane,
2,5-Dimethyl-1-(4-dimethylaminobutyl)-2,5-diaza-1-aluminacyclohexane,
2,5-Dimethyl-1-(4-dimethylaminobutyl)-2,5-diaza-1-aluminacyclopentane,
2,5-Dimethyl-1-(4-dimethylaminobutyl)-2,5-diaza-1-aluminacycloheptane,
2-Ethyl-5-propyl-1-(4-dimethylaminobutyl)-2,5-diaza-1-aluminacyclohexane,
2-Ethyl-5-propyl-1-(4-dimethylaminobutyl)-2,5-diaza-1-aluminacyclopentane,
2-Ethyl-5-propyl-1-(4-dimethylaminobutyl)-2,5-diaza-1-aluminacycloheptane,
2,5-Dimethyl-1-(3-dimethylaminopropyl)-2,5-diaza-1-gallacyclopentane,
2,5-Dimethyl-1-(3-dimethylaminopropyl)-2,5-diaza-1-gallacyclohexane,
2,5-Dimethyl-1-(3-dimethylaminopropyl)-2,5-diaza-1-gallacycloheptane,
2,5-Dimethyl-1-(3-dimethylaminopropyl)-2,5-diaza-1-gallacyclopentane,
2,5-Dimethyl-1-(3-dimethylaminopropyl)-2,5-diaza-1-gallacyclohexane,
2,5-Dimethyl-1-(3-dimethylaminopropyl)-2,5-diaza-1-gallacycloheptane,
2,5-Diethyl-1-(3-dimethylaminopropyl)-2,5-diaza-1-gallacyclohexane,
2,5-Diethyl-1-(3-dimethylaminopropyl)-2,5-diaza-1-gallacyclopentane,
2,5-Diethyl-1-(3-dimethylaminopropyl)-2,5-diaza-1-gallacycloheptane,
2,5-Diethyl-1-(4-dimethylaminobutyl)-2,5-diaza-1-gallacyclohexane,
2,5-Diethyl-1-(4-dimethylaminobutyl)-2,5-diaza-1-gallacyclopentane,
2,5-Diethyl-1-(4-dimethylaminobutyl)-2,5-diaza-1-gallacycloheptane,
2-Ethyl-5-propyl-1-(4-dimethylaminobutyl)-2,5-diaza-1-gallacyclohexane,
2-Ethyl-5-propyl-1-(4-dimethylaminobutyl)-2,5-diaza-1-gallacyclopentane,
2-Ethyl-5-propyl-1-(4-dimethylaminobutyl)-2,5-diaza-1-gallacycloheptane,
2,5-Dimethyl-1-(3-dimethylaminopropyl)-2,5-diaza-1-indacyclopentane,
2,5-Dimethyl-1-(3-dimethylaminopropyl)-2,5-diaza-1-indacyclohexane,
2,5-Dimethyl-1-(3-dimethylaminopropyl)-2,5-diaza-1-indacycloheptane,
2,5-Dimethyl-1-(3-dimethylaminopropyl)-2,5-diaza-1-indacyclopentane,
2,5-Dimethyl-1-(3-dimethylaminopropyl)-2,5-diaza-1-indacyclohexane,
2,5-Dimethyl-1-(3-dimethylaminopropyl)-2,5-diaza-1-indacycloheptane,
2,5-Dimethyl-1-(3-dimethylaminopropyl)-2,5-diaza-1-indacyclohexane,
2,5-Dimethyl-1-(3-dimethylaminopropyl)-2,5-diaza-1-indacyclopentane,
2,5-Dimethyl-1-(3-dimethylaminopropyl)-2,5-diaza-1-indacycloheptane,
2,5-Diethyl-1-(3-dimethylaminobutyl)-2,5-diaza-1-indacyclohexane,
2,5-Diethyl-1-(3-dimethylaminobutyl)-2,5-diaza-1-indacyclopentane,
2,5-Diethyl-1-(3-dimethylaminobutyl)-2,5-diaza-1-indacycloheptane,
2-Ethyl-5-propyl-1-(4-dimethylaminobutyl)-2,5-diaza-1-indacyclohexane,
2-Ethyl-5-propyl-1-(4-dimethylaminobutyl)-2,5-diaza-1-indacyclopentane or
2-Ethyl-5-propyl-1-(4-dimethylaminobutyl)-2,5-diaza-1-indacycloheptane.

7. A process according to claim 1, wherein in the catalyst system the compound of formula II is
5-Methyl-1-galla-5-azacyclooctane,
1,5-Dimethyl-1-galla-5-azacyclooctane,
1,5-Diethyl-1-galla-5-azacyclooctane,
1,5-Dipropyl-1-galla-5-azacyclooctane,
1,5-Dimethyl-1-alumina-5-azacyclooctane,
1,5-Diethyl-1-alumina-5-azacyclooctane,
1,5-Diisopropyl-1-alumina-5-azacyclooctane,
1,5-Dibutyl-1-alumina-5-azacyclooctane,
1-Methyl-5-ethyl-1-galla-5-azacyclooctane,
1-Ethyl-5-methyl-1-alumina-5-azacyclooctane,
1,6-Dimethyl-1-galla-6-azacyclodecane,
1,6-Dimethyl-1-alumina-6-azacyclodecane,
1,6-Diethyl-1-galla-6-azacyclodecane,
1,4-Dimethyl-1-galla-4-azacyclohexane,
1,6-Diethyl-1-alumina-6-azacyclodecane,
1-Galla-5-azabicyclo[3.3.3]undecane,
1-Galla-4-azabicyclo[2.2.2]octane,
1-Alumina-5-azabicyclo[3.3.3]undecane,
1-Alumina-4-azabicyclo[2.2.2]octane,
1-Galla-6-azabicyclo[4.4.4]tetradecane,
1-Alumina-6-azabicyclo[4.4.4]tetradecane,
1,5-Dimethyl-1-inda-5-azacyclooctane,
1,5-Diethyl-1-inda-5-azacyclooctane,
1,5-Dipropyl-1-inda-5-azacyclooctane,
1,5-Diisopropyl-1-inda-5-azacyclooctane,
1,5-Dibutyl-1-inda-5-azacyclooctane,
1-Methyl-5-ethyl-1-inda-5-azacyclooctane,
1-Ethyl-5-propyl-1-inda-5-azacyclooctane,
1,6-Dimethyl-1-inda-6-azacyclodecane,
1,6-Diethyl-1-inda-6-azacyclodecane,
1,4-Dimethyl-1-inda-4-azacyclohexane,
1-Inda-5-azabicyclo[3.3.3]undecane,
1-Inda-4-azabicyclo[2.2.2]octane,
1-Methyl-5-cyclohexyl-1-inda-5-azacyclooctane,
1-Methyl-5-phenyl-1-inda-5-azacyclooctane,
1-Inda-6-azabicyclo[4.4.4]tetradecane,
1,6-Dimethyl-1-galla-6-azacyclodecane,
1,6-Diethyl-1-galla-6-azacyclodecane,
1,6-Dipropyl-1-galla-6-azacyclodecane,
1,6-Diisopropyl-1-galla-6-azacyclodecane,
1,6-Dibutyl-1-galla-6-azacyclodecane,
1,6-Di-tert-butyl-1-galla-6-azacyclodecane,
1,6-Diisobutyl-1-galla-6-azacyclodecane,
1,4-Dimethyl-1-galla-4-azacyclohexane,
1,4-Diethyl-1-galla-4-azacyclohexane,
1,4-Dipropyl-1-galla-4-azacyclohexane,
1,4-Diisopropyl-1-galla-4-azacyclohexane,
1,4-Dibutyl-1-galla-4-azacyclohexane,
1,4-Diisobutyl-1-galla-4-azacyclohexane,
1,4-Di-tert-butyl-1-galla-4-azacyclohexane,
1-Methyl-5-ethyl-1-galla-5-azacyclooctane,
1-Methyl-5-propyl-1-galla-5-azacyclooctane,
1-Propyl-5-methyl-1-galla-5-azacyclooctane,
1-Ethyl-5-methyl-1-galla-5-azacyclooctane,
1-Ethyl-6-propyl-1-galla-6-azacyclodecane,
1-Propyl-6-butyl-1-galla-6-azacyclodecane,
1-Methyl-6-ethyl-1-galla-6-azacyclodecane,
1-Methyl-4-ethyl-1-galla-4-azacyclohexane,
1-Propyl-4-methyl-1-galla-4-azacyclohexane, or 1Ethyl-4-butyl-1-galla-4-azacyclohexane.

8. A process according to claim 1, wherein in the coordination catalyst system the compound of formula I or II is an organoaluminum compound.

9. A process according to claim 1, wherein in the coordination catalyst the organoaluminum compound is 1-alumina-1-(3-dimethylaminopropyl)cyclohexane or 1,5-dimethyl-1-alumina-5-azacyclooctane.

* * * * *